US011439299B2

(12) United States Patent
Weinreich et al.

(10) Patent No.: US 11,439,299 B2
(45) Date of Patent: Sep. 13, 2022

(54) SELECTION AID FOR SELECTING LENSES FOR SPECTACLES

(71) Applicant: Carl Zeiss Vision International GmbH, Aalen (DE)

(72) Inventors: Manuela Weinreich, Aalen (DE); Frank Mielich, Lauchheim (DE); Sarah Gothe, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 313 days.

(21) Appl. No.: 16/816,670

(22) Filed: Mar. 12, 2020

(65) Prior Publication Data
US 2020/0292845 A1    Sep. 17, 2020

(30) Foreign Application Priority Data

Mar. 15, 2019   (DE) ..................... 20 2019 101 497.0

(51) Int. Cl.
*A61B 3/00*      (2006.01)
*A61B 3/02*      (2006.01)
*G02C 7/02*      (2006.01)
*G02C 13/00*     (2006.01)

(52) U.S. Cl.
CPC .............. *A61B 3/0033* (2013.01); *A61B 3/02* (2013.01); *G02C 7/027* (2013.01); *G02C 13/003* (2013.01)

(58) Field of Classification Search
CPC ......... A61B 3/00; A61B 3/028; A61B 3/0033; A61B 3/0041; A61B 3/005; A61B 3/0075; A61B 3/02; A61B 3/09; A61B 3/18; G02C 7/027; G02C 13/003; G02C 7/02; G02C 7/024
See application file for complete search history.

(56) References Cited

U.S. PATENT DOCUMENTS

| 2,036,337 A | * | 4/1936 | Knapp | ..................... A61B 3/00 |
| | | | | 351/218 |
| 2005/0105050 A1 | * | 5/2005 | Hosoi | .................. A61B 3/0325 |
| | | | | 351/235 |
| 2015/0022782 A1 | * | 1/2015 | Hofeldt | .................. A61B 3/032 |
| | | | | 351/239 |

* cited by examiner

*Primary Examiner* — Jordan M Schwartz
(74) *Attorney, Agent, or Firm* — Tautz & Schuhmacher LLC; Georg Hasselmann

(57) ABSTRACT

A selection aid for selecting lenses for spectacles on the basis of a plurality of customer-specific criteria contains a first disc and a second disc. The first disc has a selection area with criteria to be selected and selection recommendations and is divided into selection regions of equal size. The second disc is rotatably connected to the first disc about an axis of rotation. The second disc partly conceals the selection area and visually frees an area region of the selection area that corresponds to one of the selection regions in terms of size and shape.

15 Claims, 5 Drawing Sheets

SELECTION AID FOR SELECTING LENSES FOR SPECTACLES

CROSS REFERENCE TO RELATED APPLICATIONS

This application claims priority to German application DE 20 2019 101 497.0 filed on Mar. 15, 2019, which is hereby incorporated by reference in its entirety.

TECHNICAL FIELD

The disclosure relates to a selection aid for selecting lenses for spectacles.

BACKGROUND

Spectacle lenses are usually selected by means of an anamnesis, wherein a trained optician, on the basis of a catalogue of questions, determines the criteria for the spectacle lens type suitable for the respective customer. The anamnesis aims to cover all possible criteria that are necessary for the proposal of the best suited spectacle lens type. As a result, the anamnesis is often very comprehensive and time-intensive. An anamnesis standard stipulating an order or weighting of questions to be asked of the customer is not commonplace, however. Moreover, there are many criteria, in particular design-related criteria, which are difficult to identify especially for new customers. Finally, a high degree of specialist knowledge and experience is required for a thorough anamnesis. Although trained opticians have sufficient specialist knowledge and experience, they are not available, in particular internationally, in every store that offers spectacles. Therefore, the anamnesis means available at the present time, in particular EDP programs for anamnesis and anamnesis questionnaires, cannot be handled well enough by every customer advisor.

SUMMARY

It is therefore an object of the disclosure to provide a selection aid for selecting lenses for spectacles which is easy to employ even without profound specialist knowledge.

This object is achieved by means of a selection aid for selecting lenses for spectacles on the basis of a plurality of customer-specific criteria including a first disc, which has a selection area, and a second disc connected to the first disk. Further aspects of the selection aid are discussed in detail below.

The concept underlying the disclosure is, on the basis of the two discs rotatable relative to one another about the axis of rotation, that of opening up the possibility, even for unpracticed personnel, of defining selection criteria on the basis of simple questions to the customer, which selection criteria can be used as a basis for reliably deriving recommendations for the spectacle lens type to be selected. By rotating the second disc relative to the first disc, a selection region having a central selection field provided with a customer-specific criterion can be selected. The latter is assigned a question, in particular a question about the age of the customer. Each of the central selection fields then has an age range, wherein the age ranges do not mutually overlap. The two discs are rotated relative to one another such that the second disc frees the selection region in whose central selection field the correct indication concerning the age of the customer is situated. Proceeding from this, in the radial direction, that is to say in the direction away from the axis of rotation, the questions assigned to the further selection fields are answered successively, and the corresponding partial selection field of the selection field to which the question is assigned is selected. Finally, a partial selection field of the last selection field is reached, which is adjoined in the radial direction by a recommendation field, which contains a recommendation for the spectacle lens type to be selected and can additionally contain a recommendation for a near addition for the spectacle lenses, which can consist in particular in a recommendation for the change of the near addition of the customer's current spectacle lenses. In particular, one of the questions assigned to the further selection fields can relate to visual challenges or difficulties of the customer, while another question assigned to the further selection fields can relate to spectacle lenses currently used by the customer. The partial selection fields of the relevant further selection fields then stipulate answers to the respective question, which the user can select to eventually arrive at the appropriate recommendation field.

BRIEF DESCRIPTION OF THE DRAWINGS

The disclosure is explained in greater detail below on the basis of an exemplary embodiment illustrated schematically in the drawings, wherein.

DESCRIPTION OF EXEMPLARY EMBODIMENTS

Figure 1A:
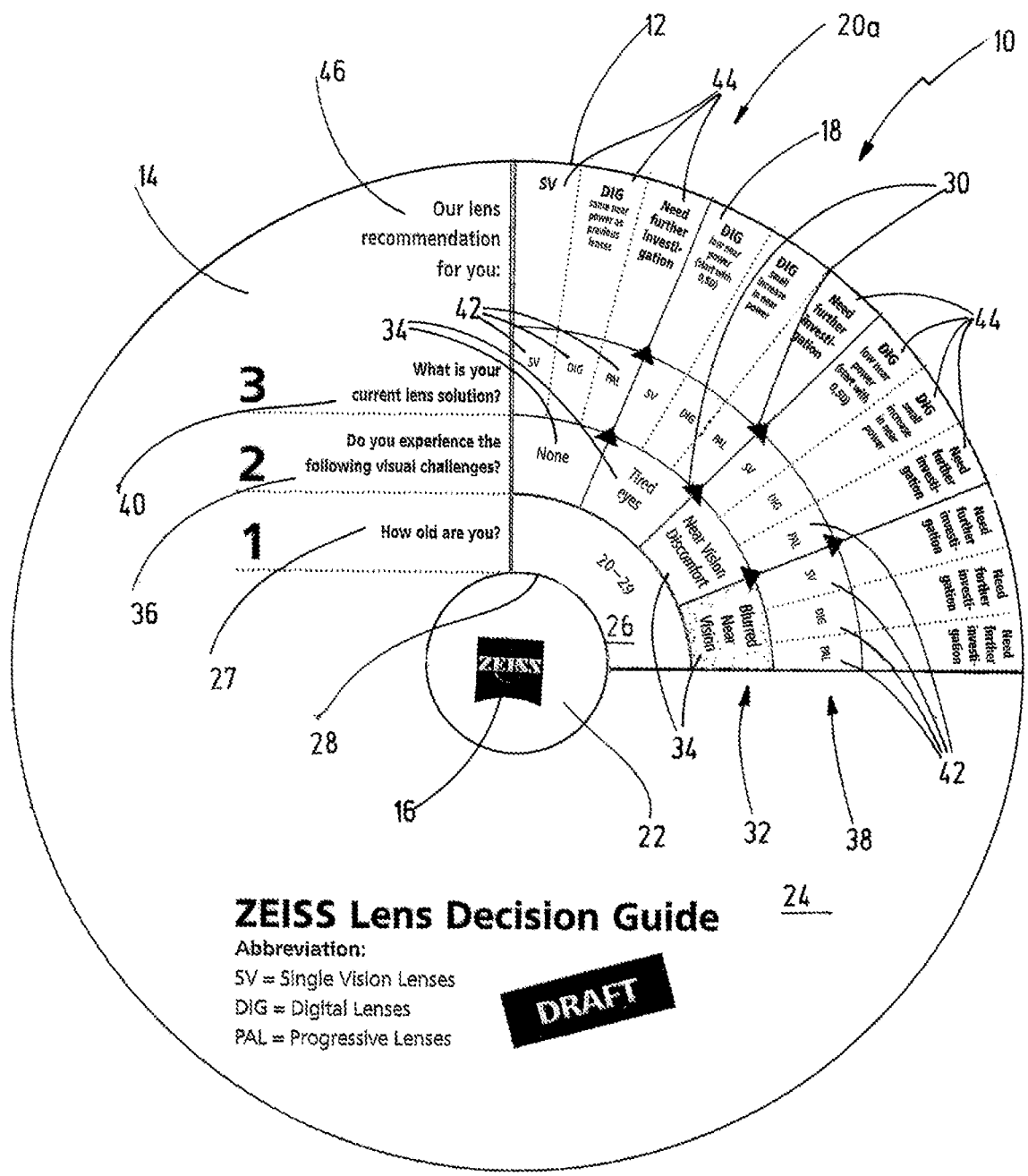
FIG. 1A shows a selection aid in a front view in a first of four different positions of the second disc relative to the first disc.

The selection aid 10 illustrated in the drawing has a first disc 12 having a circular shape, to which a second disc 14 of the same diameter is connected rotatably about an axis 16 of rotation. Both discs 12, 14 are arranged concentrically, wherein the second disc 14 is arranged on a selection area 18 of the first disc and covers the latter for the most part. The selection area 18 is subdivided into four selection regions 20a-20d, which in each case are of equal size and extend over a center point angle of 90°. The second disc 14 has the shape of a circle sector which extends over a center point angle of 270° and thus leaves free an area corresponding to one of the selection regions 20a-20d in terms of its shape and size. The two discs 12, 14 can thus be rotated relative to one another such that one of the selection regions 20a-20d is always freed visually, while the other selection regions 20a-20d are covered by the second disc 14 and are not visible. In addition, a cover disc 22 is fixedly connected to the second disc 14, the cover disc being arranged on the outer side 24 of the second disc 14 facing away from the first disc 12. The cover disc in turn has a circular shape and is concentric with respect to the first disc 12 and with respect to the second disc 14, such that its center point also lies at the axis 16 of rotation. A logo of the Applicant is arranged on the cover disc 22, the axis 16 of rotation also extending through the logo.

Figure 1B:
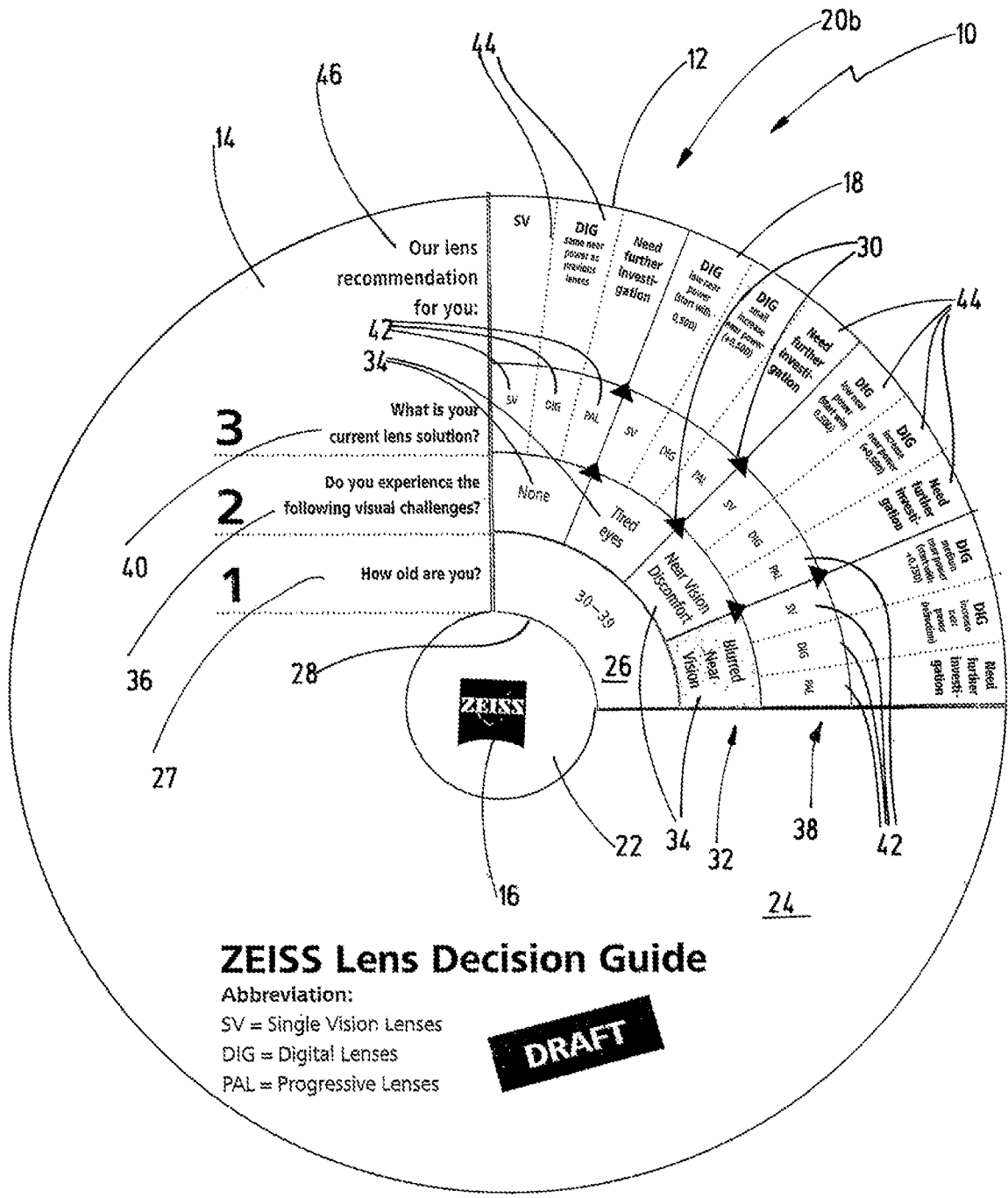
FIG. 1B shows a selection aid in a front view in a second of four different positions of the second disc relative to the first disc.
Figure 1C:
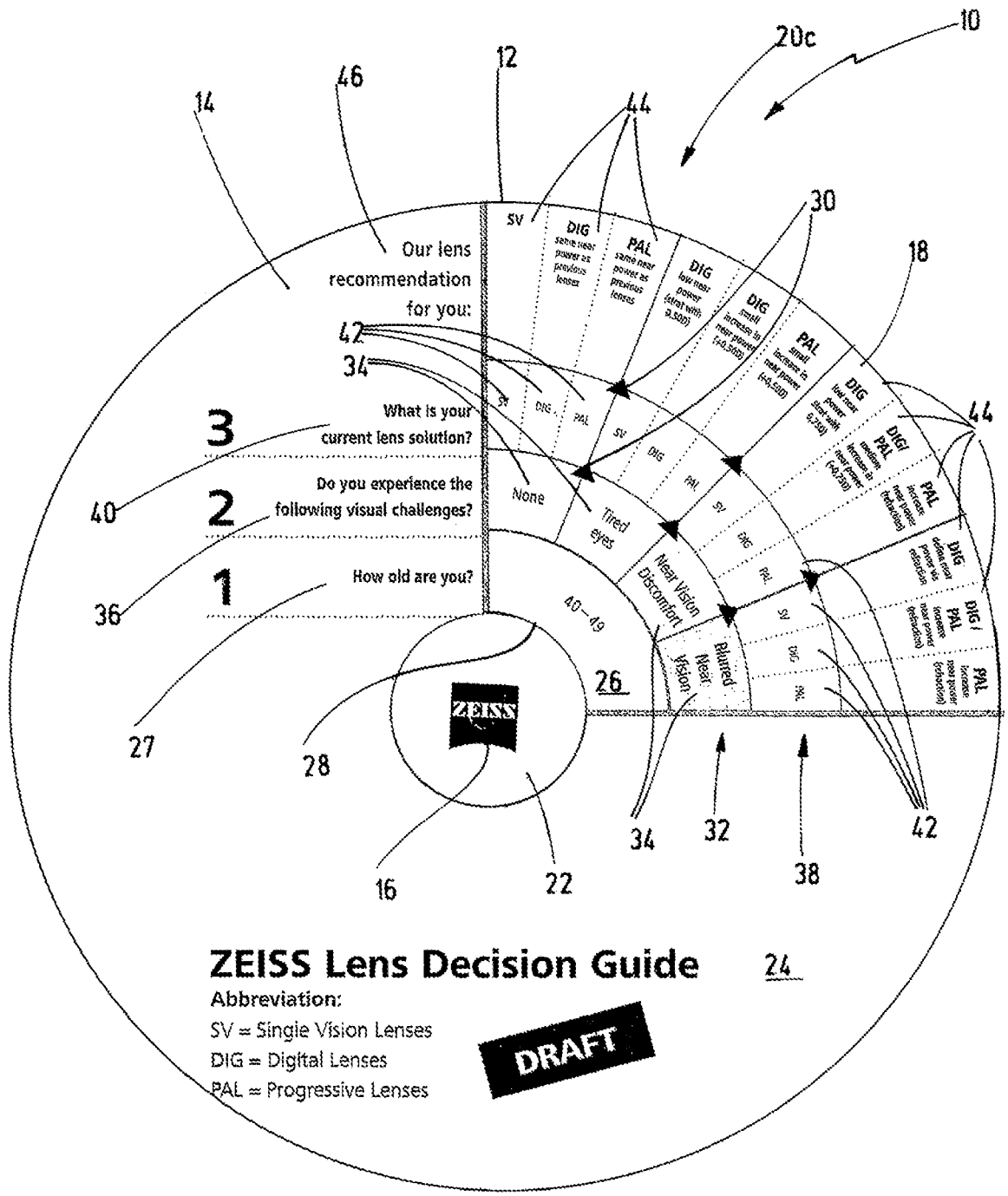
FIG. 1C shows a selection aid in a front view in a third of four different positions of the second disc relative to the first disc.
Figure 1D:
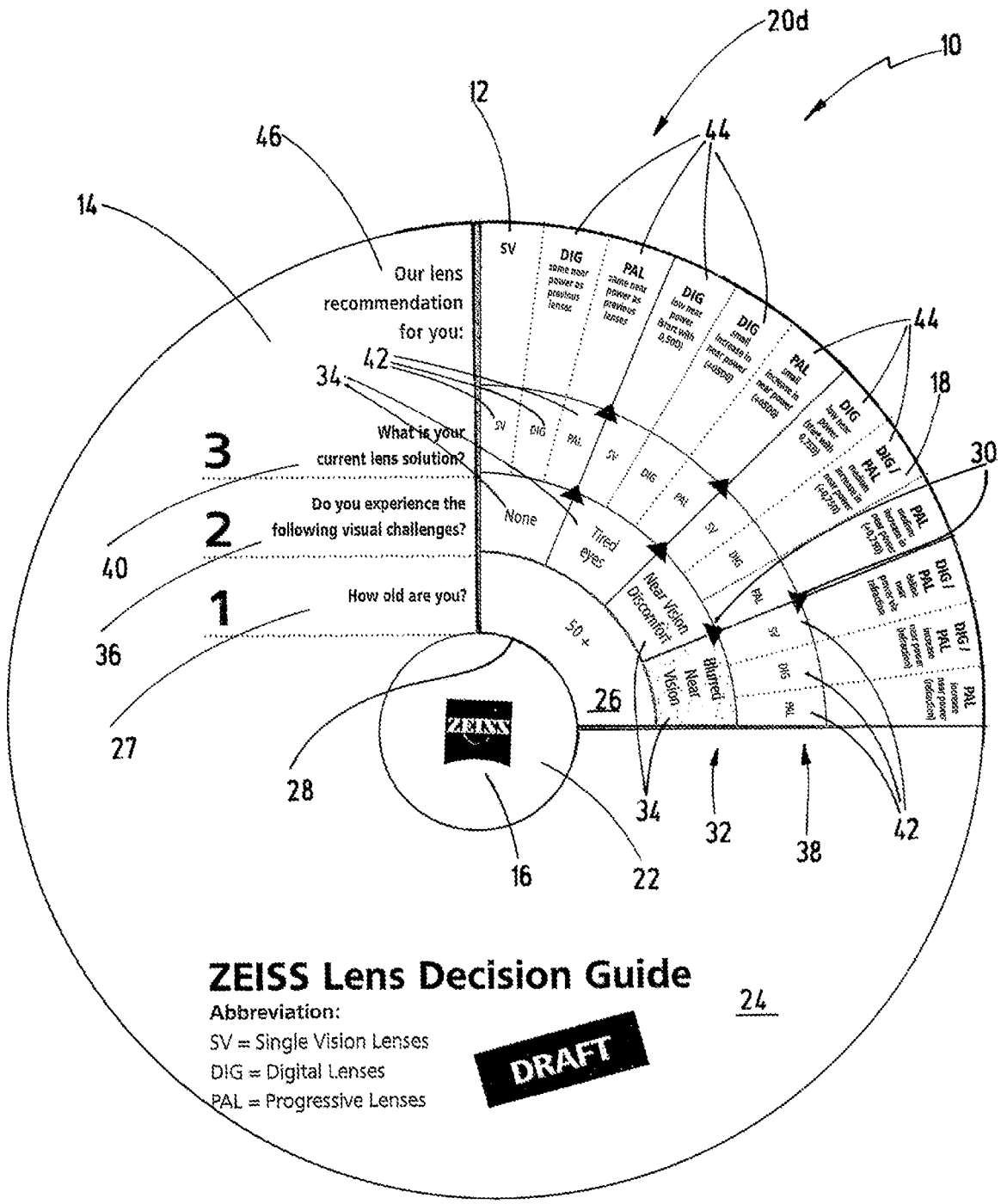
FIG. 1D shows a selection aid in a front view in a fourth of four different positions of the second disc relative to the first disc.

Each of the selection regions 20a-20d has a central selection field 26 having the shape of a sector of an annulus, the inner boundary line 28 of which in the shape of an arc coincides with the contour of the cover disc 22. Each of the central selection fields 26 is provided with a different age range of the customer; thus the age range of 20 to 29 years old in FIG. 1A, of 30 to 39 years old in FIG. 1B, of 40 to 49 years old in FIG. 1C, and of 50 years old or more in FIG. 1D. On the outer side 24 of the second disc 14, by means of corresponding positioning relative to the axis 16 of rotation, the central selection fields 26 are assigned a first question 27 about the age of the customer (How old are you?). This is the first selection criterion. After the question asked by the customer advisor has been answered, the first and second disc 12, 14 are rotated with respect to one another such that the selection region 20a-20d having the correct answer to the question is visible, while the other selection regions 20a-20d are concealed by the second disc 14.

In a radial direction 30 illustrated by arrows, that is to say away from the axis 16 of rotation, in each of the selection regions 20a-20d a first further selection field 32 is adjacent to the central selection field 26, the first further selection field in turn being subdivided into four partial selection fields 34 of equal size, which each have the shape of a sector of an annulus. At a corresponding distance from the axis 16 of rotation, the second disc 14 has a second question 36 assigned to the first further selection field 32, the second question relating to the visual challenges or difficulties of the customer (Do you experience the following visual challenges?). Each partial selection field 34 of the first further selection field 32 contains a possible answer, wherein the arrangement of the partial selection fields 34 of the first further selection field 32 is identical in each of the selection regions 20a-20d. The customer informs the customer advisor of which of the stipulated answers applies best to the question (None or Tired eyes or Near Vision Discomfort or Blurred Near Vision). In the radial direction 30, a second further selection field 38 is adjacent to the first further selection field 32, the second further selection field in turn having the shape of a sector of an annulus. Proceeding from the answer to the second question 36, the customer advisor asks the customer the third question 40, which, by virtue of corresponding arrangement on the outer side 24 of the second disc 14, is assigned to the second further selection field 38 (What is your current lens solution?) and relates to the current spectacle lens solution or the current spectacle lens type. Each of the partial selection fields 34 of the first further selection field 32 is assigned three partial selection fields 42 of the second further selection field 38, which are to be selected on the basis of the correct answer to the third question 40 and accordingly relate to the current spectacle lens solution or the current spectacle lens type. The answers SV denoting Single Vision Lenses, DIG denoting Digital Lenses and PAL denoting Progressive Lenses are available for selection. Once the appropriate partial selection field 42 of the second further selection field 38 has also been selected, then the answer to the question about the appropriate spectacle lens type can be read off in a recommendation field 44, which in turn has the shape of a sector of an annulus and in the radial direction 30 is directly adjacent to the selected partial selection field 42 of the second further selection field 38. In this case, it is possible that the suitable spectacle lens type is mentioned in the recommendation field 44, that a recommendation for the power of the spectacle lenses for the near range (near addition) is additionally given or that no clear recommendation is possible, this being indicated by "Need further investigation." The fact that the text in the recommendation fields 44 is the spectacle lens recommendation is clarified by an explanatory text 46 on the outer side 24 of the second disc 14, the explanatory text being assigned to the recommendation fields 44 by virtue of corresponding distance from the axis 16 of rotation.

Figure 2:
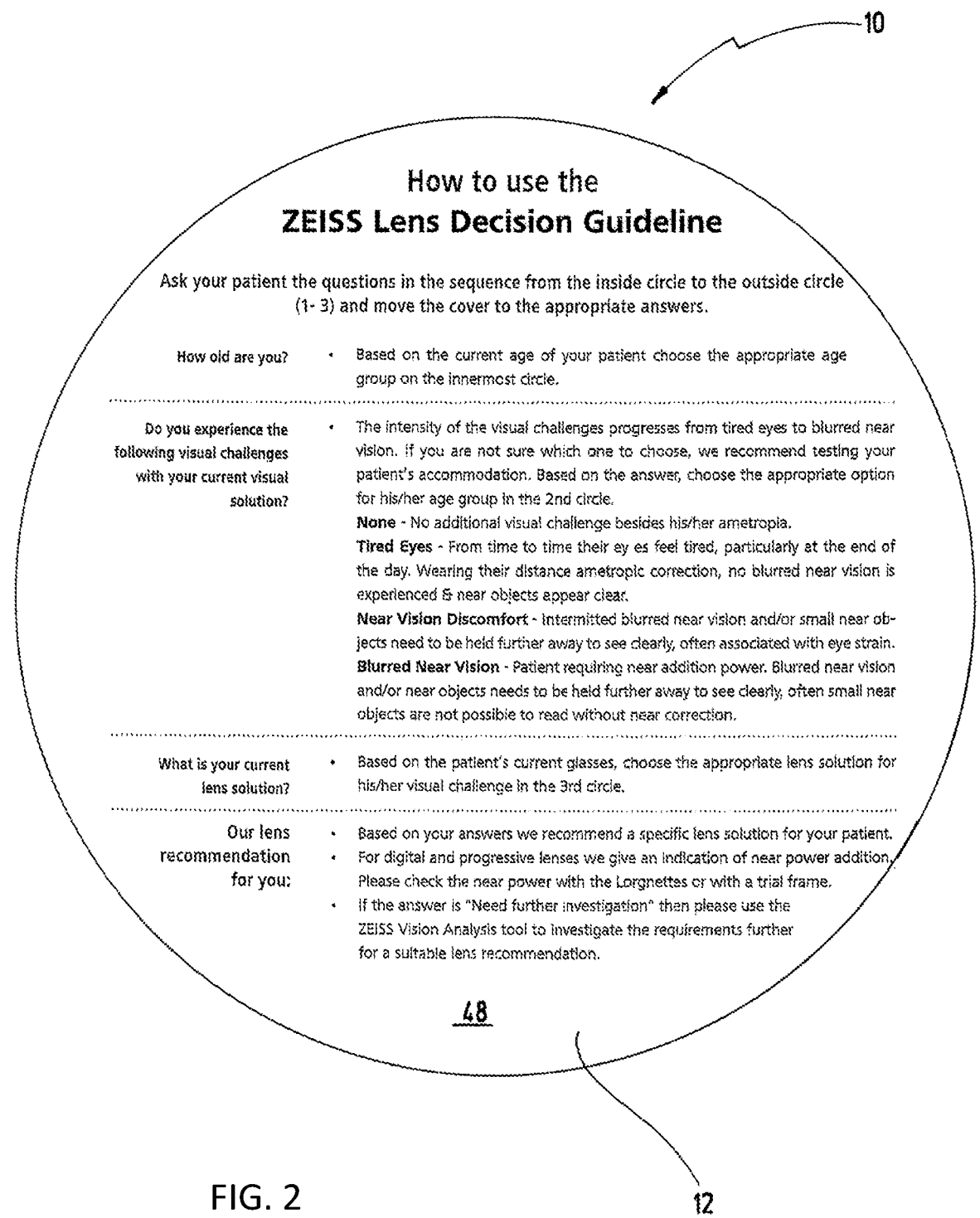
FIG. 2 shows the selection aid in accordance with FIGS. 1A to 1D in a rear view.

FIG. 2 additionally shows that operating instructions for the selection aid 10 are printed on the rear side 48 of the first disc 12 facing away from the second disc 14.

The exemplary embodiment shown assigns the question about the age of the customer to the central selection fields 26, wherein four possible age ranges can be selected. It goes without saying that this should be considered to be merely by way of example. For one thing, more or fewer age ranges can be selectable by way of corresponding extension of the selection regions 20a-20d. In this regard, each of the selection regions 20a-20d extends over a center point angle of 120° in the case of three selectable age ranges, over a center point angle of 72° in the case of five selectable age ranges, over a center point angle of 60° in the case of six selectable age ranges, etc. For another thing, the first question 27 can also relate to a different criterion, and the order of the questions can likewise be a different order.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS

10 Selection aid
12 First disc
14 Second disc
16 Axis of rotation
18 Selection area
20a-20d Selection regions
22 Cover disc
24 Outer side
26 Central selection field
27 First question
28 Inner boundary line
30 Radial direction
32 First further selection field
34 Partial selection fields
35 Second question
38 Second further selection field
40 Third question
42 Partial selection fields
44 Recommendation fields 46 Explanatory text
48 Rear side

The invention claimed is:

1. A selection aid for selecting lenses for spectacles on a basis of a plurality of customer-specific criteria, the selection aid comprising:
   a first disc having a selection area containing a criterion to be selected and a selection recommendation, the selection area being divided into a plurality of selection regions of equal size; and
   a second disc being rotatably connected to the first disc about an axis of rotation, the second disc being configured to partly conceal the selection area and to visually free an area region of the selection area that corresponds in size and shape to one of the selection regions,
   wherein each selection region widens in a radial direction proceeding from the axis of rotation outward and has a central selection field, which is provided with a customer-specific criterion, and n further selection fields following the central selection field in the radial direction,
   wherein n is a natural number,
   wherein in each selection region the n further selection fields each have a plurality of partial selection fields arranged next to one another transversely with respect to the radial direction and provided in each case with the customer-specific criterion,
   wherein in each selection region a plurality of partial selection fields follows in the radial direction the central selection field or a respective further selection field and adjoins the central selection field or the respective further selection field with the exception of the partial selection field of an n-th selection field,
   wherein in each selection region a recommendation field having the selection recommendation adjoins each of the partial selection fields of the n-th selection field in the radial direction,
   wherein the second disc has n+1 questions on an outer side thereof and facing away from the first disc, and
   wherein exactly one question each is assigned to the central selection field and to each of the further selection fields of each selection region arranged in the area region and visually free from the second disc.

2. The selection aid according to claim 1, wherein the first disc has a circular shape.

3. The selection aid according to claim 2, wherein the second disc has a shape of a circle sector.

4. The selection aid according to claim 2, wherein the first disc and the second disc have a same radius.

5. The selection aid according to claim 3, wherein each of the selection regions extends over a center point angle of 60°, 72°, 90°, or 120°.

6. The selection aid according to claim 1, wherein the question assigned to the central selection field relates to an age of the customer,
   wherein each of the central selection fields has an age range, and
   wherein the age ranges do not mutually overlap.

7. The selection aid according to claim 1, wherein one of the questions assigned to the further selection fields relates to a visual challenge or a visual difficulty of the customer, and
   wherein the partial selection field of the corresponding further selection field stipulates an answer to the one of the questions.

8. The selection aid according to claim 1, wherein one of the questions assigned to the further selection fields relates to spectacle lenses currently used by the customer, and
   wherein the partial selection field of the corresponding further selection field stipulates an answer to the one of the questions.

9. The selection aid according to claim 1, wherein the recommendation fields each have a recommendation for a spectacle lens type suitable for the customer.

10. The selection aid according to claim 1, wherein the n-th further selection fields of each selection region are identical for at least one natural number n.

11. The selection aid according to claim 1, wherein the second disc further comprises an explanatory text on the outer side facing away from the first disc, the explanatory text being assigned to the recommendation field of the selection region.

12. The selection aid according to claim 1, wherein the first disc further comprises instructions for use on a rear side thereof facing away from the second disc.

13. The selection aid according to claim 1, wherein the central selection fields, the partial selection fields, and the recommendation fields each have a shape of a sector of an annulus bounded by two radii and two arcs.

14. The selection aid according to claim 1, further comprising:
   a cover disc extending as far as an inner boundary line of the central selection field,
   wherein the cover disc is attached to the outer side of the second disc facing away from the first disc and is fixedly connected to the second disc.

15. The selection aid according to claim 1, wherein at least one portion of the recommendation field has a recommendation for a near addition of the spectacle lenses.

* * * * *